(12) United States Patent
Gupta et al.

(10) Patent No.: US 10,131,613 B2
(45) Date of Patent: Nov. 20, 2018

(54) ESTERIFICATION PROCESS

(71) Applicant: Reliance Industries Limited, Mumbai (IN)

(72) Inventors: Virendrakumar Gupta, Navi Mumbai (IN); Vilas Bhaskar Phapale, Kalyan (IN)

(73) Assignee: Reliance Industries Limited, Mumbai (IN)

( * ) Notice: Subject to any disclaimer, the term of this patent is extended or adjusted under 35 U.S.C. 154(b) by 0 days.

(21) Appl. No.: 15/714,657

(22) Filed: Sep. 25, 2017

(65) Prior Publication Data

US 2018/0086689 A1    Mar. 29, 2018

(30) Foreign Application Priority Data

Sep. 23, 2016    (IN) .............................. 201621032616

(51) Int. Cl.
     *C07C 67/08*      (2006.01)
     *B01J 31/02*      (2006.01)
     *C11B 3/00*      (2006.01)
     *C07C 67/03*      (2006.01)

(52) U.S. Cl.
     CPC ........... *C07C 67/08* (2013.01); *B01J 31/0258* (2013.01); *B01J 2231/49* (2013.01); *C07C 67/03* (2013.01); *C11B 3/003* (2013.01)

(58) Field of Classification Search
     CPC ......... C07C 67/03; C07C 67/08; C07C 37/72; B01J 31/0258; B01J 2231/49; C11B 3/003
     See application file for complete search history.

(56) References Cited

U.S. PATENT DOCUMENTS 3,321,439 A * 5/1967 Bollert .......................... 502/162

\* cited by examiner

*Primary Examiner* — Yaté K Cutliff
(74) *Attorney, Agent, or Firm* — Osha Liang LLP

(57) ABSTRACT

The present disclosure relates to a process of esterification in presence of a catalyst. The catalyst of the present disclosure is an aryloxy based phosphoric acid having general formula [{ArO}$_2$P(O)OH] and is represented by the structure:

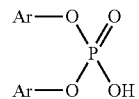

wherein, Ar represents aryl compounds.
The process of esterification is carried out by the reaction of a carboxylic acid and an alcohol in a fluid medium in the presence of the aryloxy based phosphoric acid catalyst resulting in the corresponding ester. The process of the present disclosure is simple and results in a product having a comparatively higher purity.

8 Claims, No Drawings

ESTERIFICATION PROCESS

FIELD

The present disclosure relates to an esterification process.

BACKGROUND

Esters of aliphatic alcohols and aromatic carboxylic acids are widely used in chemical industry, particularly as plasticizers and as intermediates in the preparation of polyester resins.

However, the rate of esterification reaction is usually quite slow; therefore catalysts have been used to increase the esterification reaction rate. The esterification process can be carried out using liquid catalysts such as sulfuric acid, sulfonic acid, or p-toluenesulfonic acid (liquid phase esterification reaction using liquid catalyst); a cationic ionic exchange resin as a catalyst (liquid phase esterification reaction using solid catalyst); and liquid phase acids carried by a solid carrier, and zeolite as a catalyst (gas phase esterification reaction).

Esterification reaction using sulfonic acid, hybrid inorganic solid acid material, Bronsted acidic ionic liquids, and Bronsted acid surfactant-combined catalyst (BASC) are also known in the art.

One of the problems associated with liquid-phase esterification reaction by the liquid catalyst is that the acidic liquid catalysts such as sulfuric acid or p-toluenesulfonic acid can cause corrosion problems to the reactor. These liquid acid catalysts are also discharged along with the reaction products, thus causing severe waste disposal and pollution problems. The commonly used active catalysts such as sulfuric acid, hydrochloric acid, and aluminum sulfate promote rapid reaction rates but have the serious drawback, in that they lead to considerable alcohol loss by ether formation.

Therefore, there is a need for a simple process of esterification which mitigates the drawbacks associated with the conventional processes.

OBJECTS

Some of the objects of the present disclosure, which at least one embodiment herein satisfies, are as follows:

It is an object of the present disclosure to ameliorate one or more problems of the prior art or to at least provide a useful alternative.

Another object of the present disclosure is to provide a simple process for esterification.

Still another object of the present disclosure is to provide a simple process of esterification in the presence of diaryl phosphoric acid catalyst.

Other objects and advantages of the present disclosure will be more apparent from the following description, which is not intended to limit the scope of the present disclosure.

SUMMARY

The present disclosure relates to a process of esterification in presence of a catalyst having the structure,

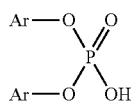

wherein Ar represents aryl compounds.

The esterification process comprises, reacting a carboxylic acid and an alcohol in a fluid medium in the presence of the diaryl phosphoric acid catalyst at a temperature in the range of 100° C. to 150° C. for a time period in the range of 8 hours to 12 hours in an inert atmosphere to obtain an ester. Typically, the catalyst can be aryloxy based phosphoric acid catalyst, typically di-aryl phosphoric acid catalyst.

DETAILED DESCRIPTION

Conventionally, the process of esterification includes use of complex catalysts, complicated methods of catalyst preparation and has limited substrate choice. There remains scope to develop an esterification reaction by using different catalyst.

The present disclosure provides a process of esterification in the presence of a catalyst. The process is described in detail hereinafter.

A carboxylic acid, and an alcohol, is reacted in a fluid medium in the presence of catalyst at a temperature in the range of 100° C. to 150° C. for a time period in the range of 8 hours to 12 hours to obtain an ester. The so obtained ester can be purified by chromatography to obtain a pure ester. The purity of the ester is at least 99%, In an embodiment, the esterification reaction of the present disclosure is a single pot reaction.

In the present disclosure, the carboxylic acid can be at least one selected from the group consisting of aliphatic carboxylic acid, and aromatic carboxylic acid. In one embodiment the carboxylic acid is an aliphatic carboxylic acid.

The alcohol can be at least one selected from the group consisting of aliphatic alcohol, and aromatic alcohol. In one embodiment the alcohol is an aromatic alcohol. In another embodiment the alcohol is an aliphatic alcohol.

Therefore, it is envisaged and within the scope of this disclosure that one or more carboxylic acids and one or more alcohols may be involved in the esterification processes.

The ratio of the amount of the carboxylic acid to the amount of alcohol is in the range of 1:1.1.

The fluid medium used in the esterification process as disclosed in the present disclosure can be toluene.

The fluid medium used in the process of esterification is used as an azeotrope to remove water from the reaction zone. The process of removal of water is a continuous step.

The process of the present disclosure includes a step of purification of the crude ester. The step of purification includes washing with a polar solvent such as ethyl acetate followed by silica gel chromatography to obtain an ester having purity of at least 95%.

The phosphoric acid catalyst can be aryloxy based phosphoric acid catalyst having the general formula [{ArO}$_2$P(O)OH] and is represented by the structure:

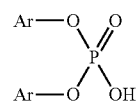

wherein Ar represents an aryl group.

In one embodiment the aryloxy phosphoric acid catalyst is diaryl phosphoric acid catalyst, typically diphenyl phosphoric acid.

The amount of the phosphoric acid catalyst used in the process of the present disclosure is in the range of 2 mol % to 8 mol % with respect to the mass of the carboxylic acid.

The diaryl phosphoric acid catalyst can be prepared from the corresponding diaryl phosphoryl chloride. The diaryl phosphoric acid catalyst can be prepared by known methods.

In one embodiment, diphenyl phosphoric acid catalyst can be prepared by hydrolyzing diphenyl phosphoryl chloride with water in acetone at 60° C. for 2 hours. After 2 hours acetone is removed by distillation, followed by quenching with water and diaryl phosphoric acid is extracted using $CHCl_3$. The organic layer ($CHCl_3$) is concentrated to obtain crude diaryl phosphoric acid catalyst. Crude diaryl phosphoric acid catalyst can be purified using silica gel based flash chromatography using a solvent system containing 80% dichloromethane in hexane.

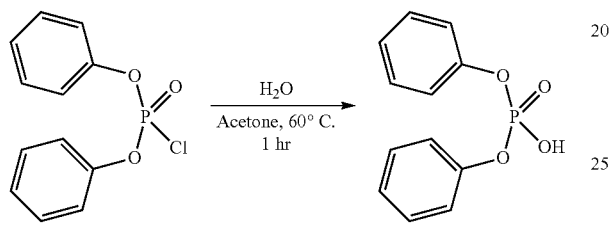

The esterification process of the present disclosure is associated with many advantages such as the process is effective, simple, economical, environment friendly, and easy.

The present disclosure is further described in light of the following laboratory scale experiments which are set forth for illustration purpose only and not to be construed for limiting the scope of the disclosure. The experiments provided herein below can be scaled up to industrial/commercial scale.

EXPERIMENTS

Experiment 1

Preparation of Benzyl Octanoate in Accordance with the Process of the Present Disclosure In a flask 2.88 gm of octanoic acid, 2.38 gm (2.278 ml) of benzyl alcohol, and 0.25 gm of diphenylphosphoric acid were placed under nitrogen atmosphere. 50 ml toluene was added in the flask under nitrogen atmosphere to obtain a mixture. The mixture was refluxed at 125° C. for 8 hours. Water formed during the reaction was separated azeotropically by using Dean-stark apparatus. The resultant mixture formed during the reaction was monitored by thin layer chromatography (TLC). After completion of the reaction (monitored by TLC), the resultant mixture was cooled to 25° C. and quenched with water to obtain a product mixture.

To separate product from the product mixture, 100 ml of ethyl acetate was added to the product mixture to obtain a biphasic system. A first organic layer, i.e. ethyl acetate was separated. The aqueous layer was further washed twice with ethyl acetate (50 ml each) followed by separation of the organic layer (second organic layer and third organic layer). The separated organic layers were combined, concentrated, and dried over anhydrous sodium sulphate to obtain a crude product.

The crude product was purified using silica gel based flash chromatography using a solvent system containing 5-10% ethyl acetate in hexane to obtain benzyl octanoate having 99% purity. The yield of the product (benzyl octanoate) was 82%.

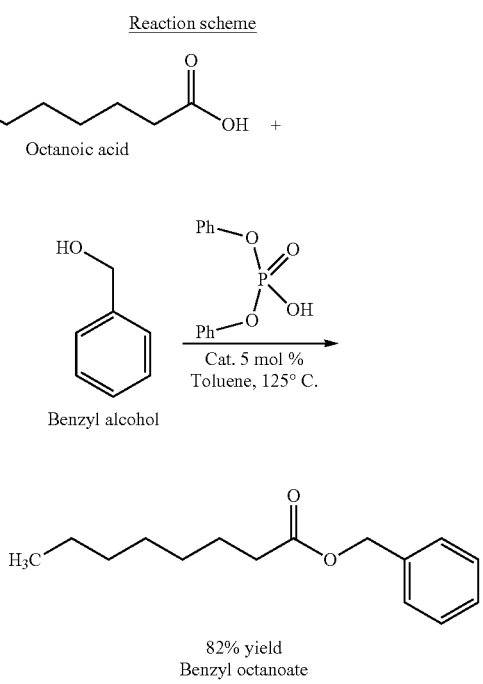

Experiment 2

Preparation of Pentyl Octanoate in Accordance with the Process of the Present Disclosure In a flask 2.88 gm of octanoic acid, 1.939 gm (2.39 ml) of pentyl alcohol, and 0.25 gm of diphenylphosphoric acid were placed under nitrogen atmosphere. 50 ml toluene was added in the flask under nitrogen atmosphere to obtain a mixture. The mixture was refluxed at 125° C. for 7 hours. Water formed during the reaction was separated azeotropically by using Dean-stark apparatus. The resultant mixture formed during the reaction was monitored by thin layer chromatography (TLC). After completion of the reaction (monitored by TLC), the resultant mixture was cooled to 25° C. and quenched with water to obtain a product mixture.

To separate product from the product mixture, 100 ml of ethyl acetate was added to the product mixture to obtain a biphasic system. A first organic layer, i.e. ethyl acetate layer was separated. The aqueous layer was further washed twice with ethyl acetate (50 ml each) followed by separation of the organic layer (second organic layer and third organic layer). The separated organic layers were combined, concentrated, and dried over anhydrous sodium sulphate to obtain a crude product.

The crude product was purified using silica gel based flash chromatography using a solvent system containing 2-5% ethyl acetate in hexane to obtain pentyl octanoate having 98% purity. The yield of the product (pentyl octanoate) was 86%.

Reaction scheme

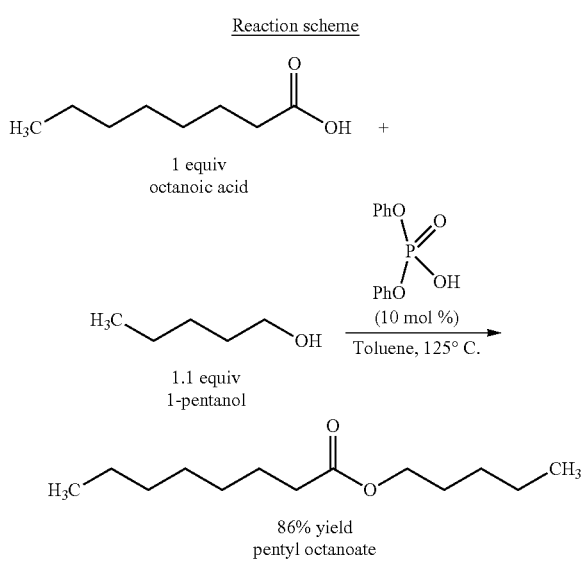

86% yield
pentyl octanoate

Experiment 3

Preparation of Dibenzyl Phthalate in Accordance with the Process of the Present Disclosure In a flask 4.15 gm of phthalic acid, 5.947 gm (5.7 ml) of benzyl alcohol, and 624 gm of diphenylphosphoric acid were placed under nitrogen atmosphere. 50 ml toluene was added in the flask under nitrogen atmosphere to obtain a mixture. The mixture was refluxed at 125° C. for 9 hours. Water formed during the reaction was separated azeotropically by using Dean-stark apparatus. The resultant mixture formed during the reaction was monitored by thin layer chromatography (TLC). After completion of the reaction (monitored by TLC), the resultant mixture was cooled to 25° C. and quenched with water to obtain a product mixture.

To separate product from the product mixture, 100 ml of ethyl acetate was added to the product mixture to obtain a biphasic system. A first organic layer, i.e. ethyl acetate layer was separated. The aqueous layer was washed twice with ethyl acetate (50 ml each) followed by separation of second and third organic layer. The separated organic layers were combined, concentrated, and dried over anhydrous sodium sulphate to obtain a crude product.

The crude product was purified using silica gel based flash chromatography using a solvent system containing 25% ethyl acetate in hexane to obtain dibenzyl phthalate having 96% purity. The yield of dibenzyl phthalate was 66%.

Reaction scheme

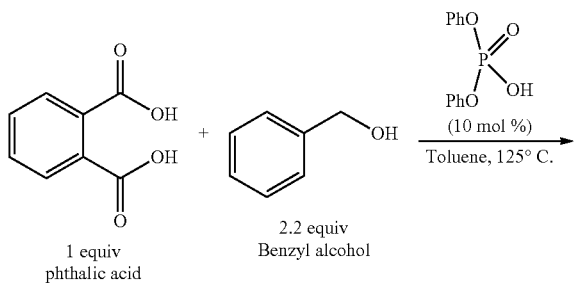

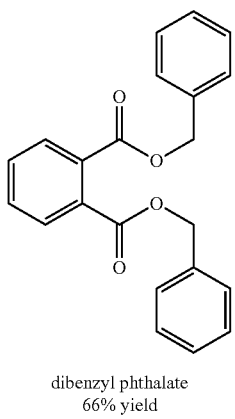

dibenzyl phthalate
66% yield

Technical Advancements and Economic Significance

The present disclosure provides several technical advancements that include, but are not limited to, the realization of:
- a simple and easy esterification process in the presence of diaryl phosphoric acid catalyst;
- a diaryl phosphoric acid catalyst that provides high yield of esterified product; and
- negligible impurity formation.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

Any discussion of documents, acts, materials, devices, articles or the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

While considerable emphasis has been placed herein on the components and component parts of the preferred embodiments, it will be appreciated that many embodiments can be made and that many changes can be made in the preferred embodiments without departing from the principles of the disclosure. These and other changes in the preferred embodiment as well as other embodiments of the disclosure will be apparent to those skilled in the art from the disclosure herein, whereby it is to be distinctly understood that the foregoing descriptive matter is to be interpreted merely as illustrative of the disclosure and not as a limitation.

The invention claimed is:

1. A process of esterification, said process comprising reacting a carboxylic acid, and an alcohol, in a fluid medium in the presence of a diphenyl phosphoric acid catalyst.

2. The process as claimed in claim 1 which is carried out at a temperature in the range of 100° C. to 150° C. for a time period in the range of 8 hours to 12 hours in an inert atmosphere.

3. The process as claimed in claim 1, wherein said carboxylic acid is at least one selected from the group consisting of aliphatic carboxylic acid, and aromatic carboxylic acid; and said alcohol is at least one selected from the group consisting of aliphatic alcohol, and aromatic alcohol.

4. The process as claimed in claim 1, wherein the amount of said catalyst is in the range of 2 mol % to 8 mol % with respect to the mass of said carboxylic acid.

5. The process as claimed in claim 1, wherein the ratio of the amount of said carboxylic acid to said alcohol is in the range of 1:1.1.

6. The process as claimed in claim 1, wherein said fluid medium is toluene.

7. The process as claimed in claim 1 includes a further step of purification by washing with a polar solvent such as ethyl acetate followed by silica gel chromatography to obtain an ester having purity of at least 95%.

8. The process as claimed in claim 1 is a single pot reaction.

* * * * *